(12) United States Patent
Lee

(10) Patent No.: US 6,547,797 B1
(45) Date of Patent: Apr. 15, 2003

(54) CIRCUMCISION CLAMP

(76) Inventor: Sang Bong Lee, 39-10 Song Jung Dong, Kangnung Shi, Kangwon Do (KR)

( * ) Notice: Subject to any disclaimer, the term of this patent is extended or adjusted under 35 U.S.C. 154(b) by 0 days.

(21) Appl. No.: 09/985,514

(22) Filed: Nov. 5, 2001

(30) Foreign Application Priority Data

Jul. 11, 2001 (KR) .......................................... 2001-41461
Oct. 10, 2001 (KR) .......................................... 2001-30833

(51) Int. Cl.⁷ ............................................. A61B 17/32
(52) U.S. Cl. ..................................................... 606/118
(58) Field of Search .............................. 606/118, 120, 606/167, 174; D24/143

(56) References Cited

U.S. PATENT DOCUMENTS 2,353,647 A * 7/1944 Carmichael .................. 606/118
5,931,843 A * 8/1999 Dunaway ..................... 606/118
D430,671 S * 9/2000 Shute ......................... D24/143

* cited by examiner

Primary Examiner—Eduardo C. Robert
(74) Attorney, Agent, or Firm—GWiPS

(57) ABSTRACT

A novel circumcision clamp which enables one to easily perform a circumcision operation without inducing bleeding and shortens the operating time is comprised of: a pair of crossed members (31, 31*a*) has handles (30) with finger loops at the proximal ends. A pivot (32) is disposed at a center of the crossed members for moving back and forth from each other about a common axis. A pair of first and second compression rings (10, 20) forms annular disk shape with a stitching means. The pair of annular disk shaped compression rings (10, 20) is integrally attached at the other proximal ends of the crossed members (31 or 31*a*) to mate parallel each other. Thus, the foreskin is able to clamp between the parallel mating surface of the annular disk shaped compression rings (10, 20). A plurality of paired stitching device is disposed on the parallel mating surface of the annular disk shaped compression rings (10, 20). The paired stitching device has a plurality of stitching cavities or holes with openings toward the periphery of annular rings. Therefore, the severed foreskin is easily sutured through the stitching devices.

15 Claims, 6 Drawing Sheets

CIRCUMCISION CLAMP

FIELD OF THE INVENTION

The present invention is related to a circumcision clamp designed to be used for surgical removal of excessive foreskin or prepuce of penis, which is covered glans. More particularly, the circumcision clamp enables one to easily perform a circumcision operation without causing bleeding and to also shorten the operation time.

BACKGROUND OF THE INVENTION

The conventional circumcision is usually performed by a surgical team consisting of a surgeon and at least one assistant. The team severs the excessive foreskin, which is covered glans of the penis and sutures the cut edge of the foreskin. The average operating time of a conventional circumcision operation consumes is approximately half an hour, a time period considered relatively long for an operation.

The conventional circumcision clamp has another disadvantage in that it causes severe bleeding during the surgery. Generally, most patients experience apprehension during a circumcision operation. During the operation, the patient's penis is almost in a naturally flaccid state. Thus, a new concept of circumcision clamp is needed to overcome the above disadvantages of using the conventional surgical clamp.

SUMMARY OF THE INVENTION

To avoid experiencing the disadvantages of conventional circumcision, a novel circumcision clamp is introduced.

An object of the present invention is to provide a circumcision clamp that would prevent bleeding by compressing the foreskin during the operation.

Another object of the present invention is to provide a circumcision clamp that would effect the shortening of the operating time of circumcision.

Therefore, a circumcision clamp of the present invention is comprised of: a pair of crossed members formed a first crossed member (31) and second crossed member (31a) having handles (30) at proximal ends, the handles (30) having a pair of finger loops (33, 33a) and clamping tabs (34) extended from the finger loops (33, 33a), and the clamping tabs (34) contain a set of angular facets (34a), a pivot (32) disposed at a center of the first and second crossed members for moving back and forth each other about a common axis, a pair of compression rings formed a first annular disk shaped compression ring (10) and second annular disk shaped compression ring (20), the first and second annular disk shaped compression rings (10, 20) integrally formed on the other proximal ends of the first and second crossed members (31, 31a), respectively to mate parallel each other, so as to clamp foreskin between parallel mating surface of the first and second annular disk shaped compression rings (10, 20), a plurality of paired stitching device having a plurality of stitching cavities or holes with openings toward the periphery of annular rings (10, 20), and the stitching device disposed on the parallel mating surface of the first annular disk shaped compression ring (10) and second annular disk shaped compression ring (20).

An alternative circumcision clamp of the present invention is comprised of: a pair of crossed members formed a first crossed member (31) and second crossed member (31a) having handles (30) at proximal ends, the handles (30) having a pair of finger loops (33, 33a) and clamping tabs (34) extended from the finger loops (33, 33a), and the clamping tabs (34) contain a set of angular facets (34a), a pivot (32) disposed at a center of the first and second crossed members for moving back and forth each other about a common axis, a pair of compression rings formed a first annular disk shaped compression ring (10) and second annular disk shaped compression ring (20), the first and second annular disk shaped compression rings (10, 20) integrally formed on the other proximal ends of the first and second crossed members (31, 31a), respectively to mate parallel each other, so as to clamp foreskin between parallel mating surface of the first and second annular disk shaped compression rings (10, 20), and the parallel mating surface of the first and second annular disk shaped compression rings (10, 20) have an anti-slip means. The anti-slip means is disposed inward of the parallel mating surface of the first and second annular disk shaped compression rings (10, 20) and comprised of a plurality of anti-slip grooves (76, 86) for preventing slipping.

BRIEF DESCRIPTION OF THE DRAWINGS

FIG. 2 shows an excessive foreskin protruding from between the first and second compression rings.

FIG. 3 shows the trimming of the excessive foreskin.

FIG. 4 shows the suturing of the cut edge of foreskin.

DETAILED DESCRIPTION OF THE INVENTION

To achieve the objects of the present invention, a new concept of circumcision clamp is designed.

Generally, a correctly sized circumcision clamp is selected for a circumcision operation depending on the patient's penis size. Therefore, a typically sized circumcision clamp is described in detail accompanying the drawings.

Figure 1:
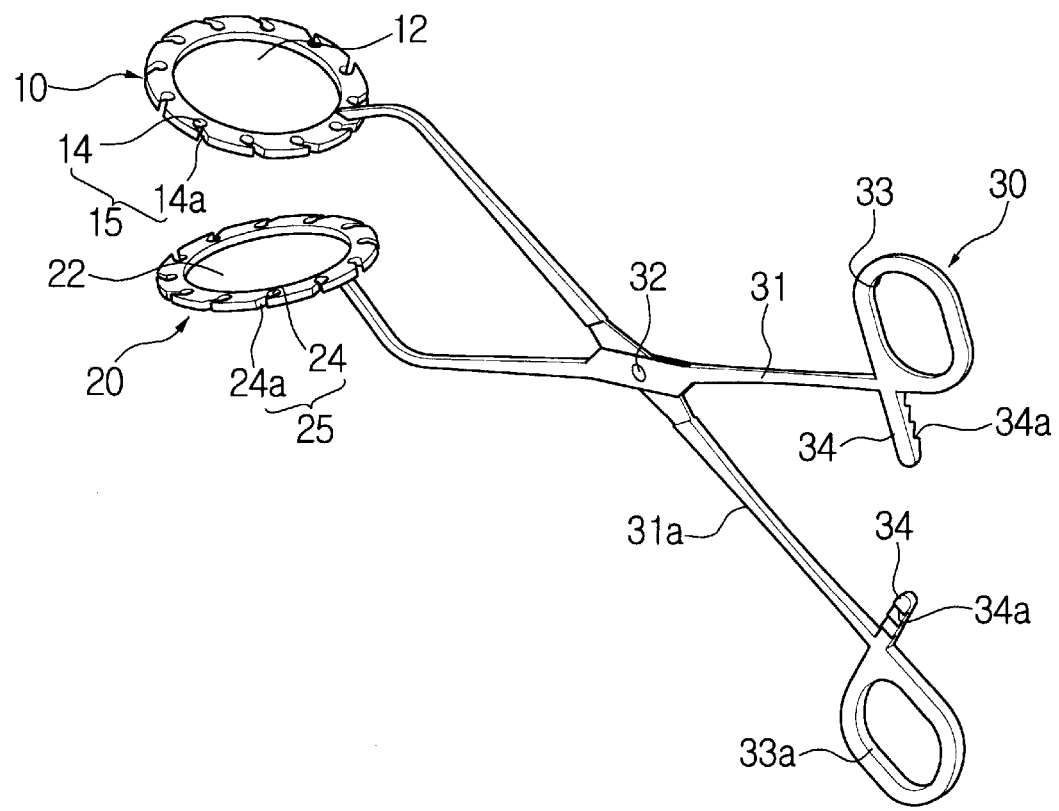
FIG. 1 represents a typical size of a circumcision clamp of the present invention.

As shown in FIG. 1, a circumcision clamp of the present invention is comprised of: a pair of crossed members forms a first crossed member (31) and second crossed member (31a) having handles (30) at proximal ends. The handles (30) have a pair of finger loops (33, 33a) and clamping tabs (34) extended from the finger loops (33, 33a). The clamping tabs (34) contain a set of angular facets (34a). A pivot (32) is disposed at a center of the first and second crossed members for moving back and forth each other about a common axis. A pair of compression rings forms a first annular disk shaped compression ring (10) and second annular disk shaped compression ring (20). The first and second annular disk shaped compression rings (10, 20) are integrally formed on the other proximal ends of the first and second crossed members (31, 31a), respectively to mate parallel each other, so as to clamp foreskin between the parallel mating surface of the first and second annular disk shaped compression rings (10, 20). A plurality of paired stitching device has a plurality of stitching cavities or holes with openings toward the periphery of annular rings (10, 20). The stitching devices are disposed on the parallel mating surface of the first annular disk shaped compression ring (10) and second annular disk shaped compression ring (20).

A plurality of paired stitching devices (15, 25) has a plurality of stitching holes (14, 24) and openings (14a, 24a) with spiral shape spiraling outward to the periphery of annular rings (10, 20). The openings (14a, 24a) are positioned at opposite positions from each other. The plurality of paired stitching devices form a plurality of wide cut out openings (74, 84) and a plurality of protruding parts (87) being disposed between the wide cut out openings (74, 84) with a certain interval. The wide cut out openings (74, 84) have a plurality of convex and concave guiding grooves (85) connecting to inner annular ring. The protruding parts (87) have anti-slip grooves (76, 86) for preventing slipping. The pair of first and second compression rings has varying sizes of outer diameter in ranges of 20~50 mm with various configurations, and the inner diameter of annular ring has varying sizes in a range of 10~40 mm.

The pair of first and second compression rings (10, 20) forms an annular disk shape with a hollow area at the center for inserting a glans penis. The first and second compression rings (10, 20) can be moved closer or further apart forth each other for clamping or releasing the foreskin by operating the handles (30).

For the first compression ring, there is a plurality of first stitching devices (15) arranged in a certain interval on the periphery of the first annular ring (10). The first stitching device (15) is comprised of a first stitching cavity or hole (14) and a first opening (14a). The first opening (14a) has a spiral shape which spirals toward the periphery of the first annular ring (10). The overall shape of the first compression ring with the stitching device (15) is similar to a zigzag circular saw.

For the second compression ring, there is a plurality of second stitching devices (25) arranged in a certain interval on the periphery of the annular ring (20). The second stitching device (25) is comprised of a second stitching hole (24) and a second opening (24a). The second opening (24a) has a spiral shape which spirals toward the periphery of second annular rings (10). The overall shape of the second compression ring with the second stitching device (25) is similar to a zigzag circular saw.

The configuration of the first and second compression rings (10, 20) is identical except that they spiral in the opposite direction of the openings. The spiral shape of the opening of the first compression ring (10) is curved counterclockwise. The spiral shape of the opening of the second compression ring (20) is curved clockwise.

The first and second compression rings (10, 20) are integrally fixed at the proximal end of opposite sides of the handles (30).

A locking device is provided for securely clamping the foreskin during a circumcision operation. A pair of clamping tabs (34) is extended from each handle (30) of the finger loops (33, 33a) in such a way that each side of the clamping tabs (34) will overlap as the handles (30) are closed. The clamping tabs (34) containing a set of angular facets (34a) are oppositely face each other for engaging the angular facets (34a) together.

While the crossed members (31, 31a) are closing, the first and second compression rings (10, 20) are approaching to clamp the foreskin.

Figure 2:
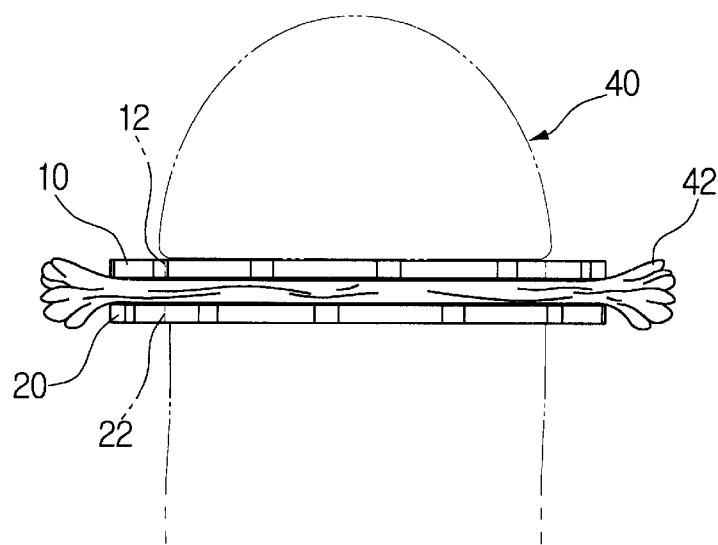
FIG. 2 to FIG. 4 represent the surgical operating process of the circumcision when using a typically sized circumcision clamp of the present invention.
Figure 3:
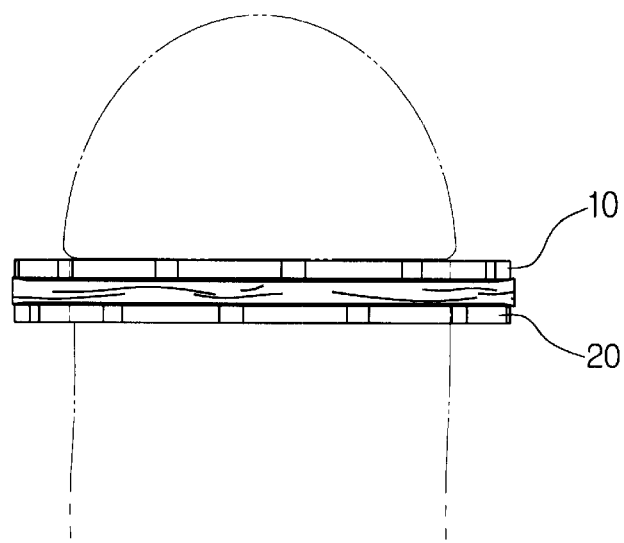
Figure 4:
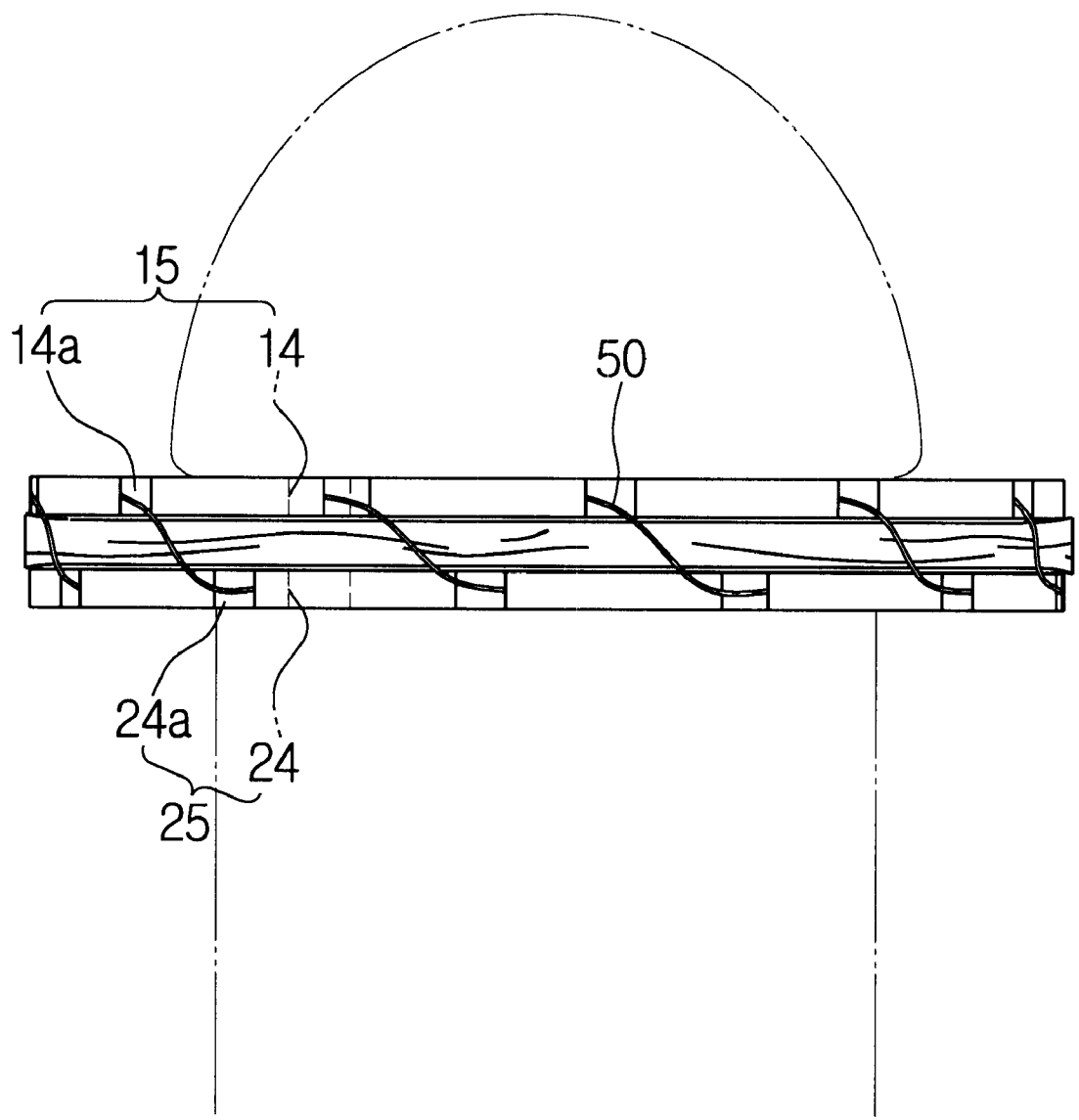

Here, a process of the circumcision operation is illustrated through FIGS. 2 to FIG. 4. FIG. 2 shows an excessive foreskin protruding from between the first and second compression rings. FIG. 3 shows a trimming of the excessive foreskin. FIG. 4 shows suturing of the cut edge of foreskin.

At first, a properly sized circumcision clamp is selected depending on the patient's penis size. Then, the patient's glans penis (40) is inserted through the hollow parts (12, 22) of annular rings. The first compression ring is positioned for exposing the entire glans. Then, the excessive foreskin (42) is spread over the first compression ring. Next, the second compression ring is slowly closed to clamp the spreading foreskin. Now, the excessive foreskin (42) is peripherally stuck out between the first and second compression rings (10, 20) as shown in FIG. 2. Next, the excessive foreskin protruding out around the compression rings is trimmed by a severance means, as shown FIG. 3. While the excessive foreskin is cutting, there would be no bleeding because the first and second compression rings (10, 20) are peripherally clamping the foreskin.

The next step is to suture the cut edge of foreskin by a proper stitching means with a thread (50), as shown in FIG. 4. The stitching is performed through the stitching cavities or holes (14, 24) of the first and second stitching devices (15, 25) by piercing the clamped foreskin. During the stitching process, the thread will pierce the foreskin and pass smoothly through the spiral opening for the nest stitching. When the thread pierces the foreskin from the upper stitch hole (14), the thread will slide out through the upper spiral opening (14a) to fold the cut edge of foreskin downward. When the thread pierces the foreskin from the bottom stitch hole (24), the thread will slide out through the bottom spiral opening (24a) to fold the cut edge of foreskin upward. The entire periphery of cut edge of foreskin of the penis (40) will be stitched by repeating the stitching process. When the stitching process is completed, the first and second compression rings (10, 20) would be released by disengaging the clamping tabs (34).

Figure 5:
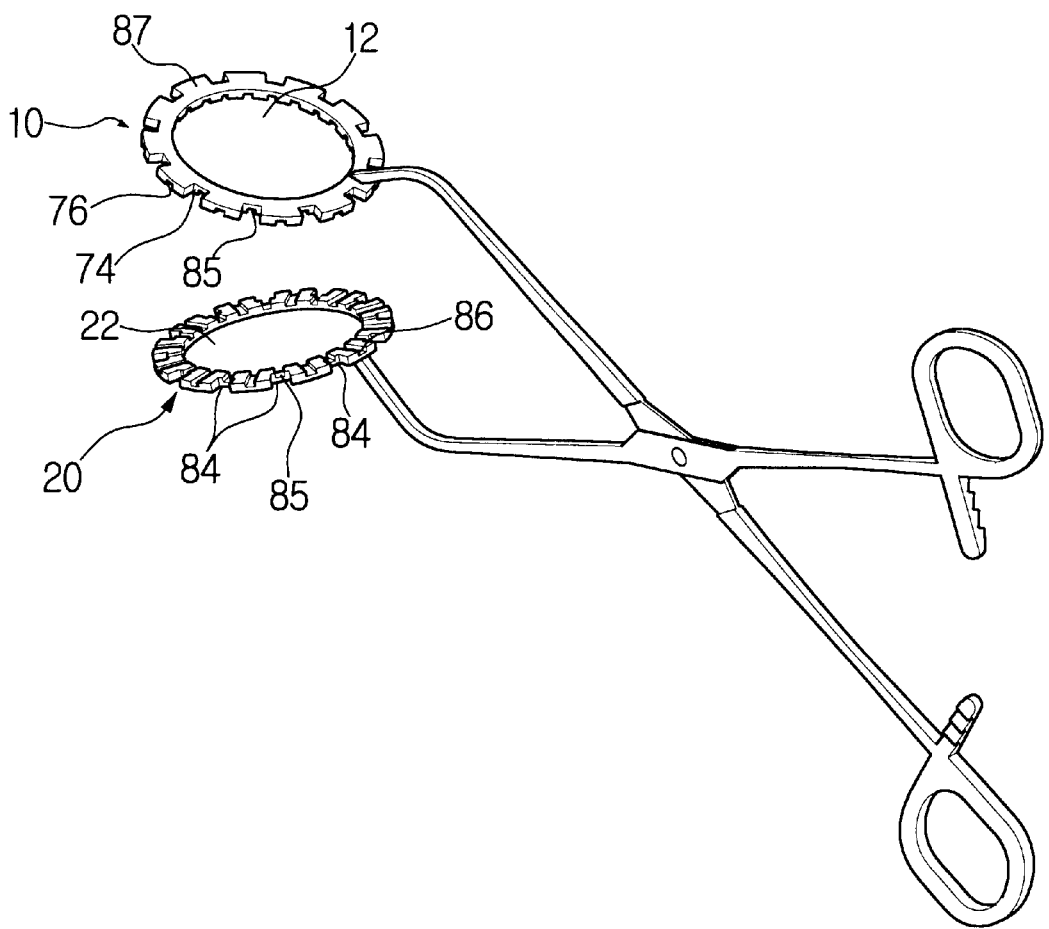
FIG. 5 is another embodiment of the invention.

FIG. 5 illustrates another embodiment of the present invention. In this embodiment, the first and second stitching devices (15, 25) formed at the first and second compression rings (10, 20) is comprised of a plurality of widely cut out openings (74, 84) with a plurality of convex and concave guiding grooves (85) connected to an inner annular ring. A plurality of protruding parts (87) linear shaped anti-slip grooves (76, 86) is disposed between the widely cut out openings (74, 84). The anti-slip grooves (76, 86) preferably have inclining shape grooves rather than a linear shapes.

Figure 6:
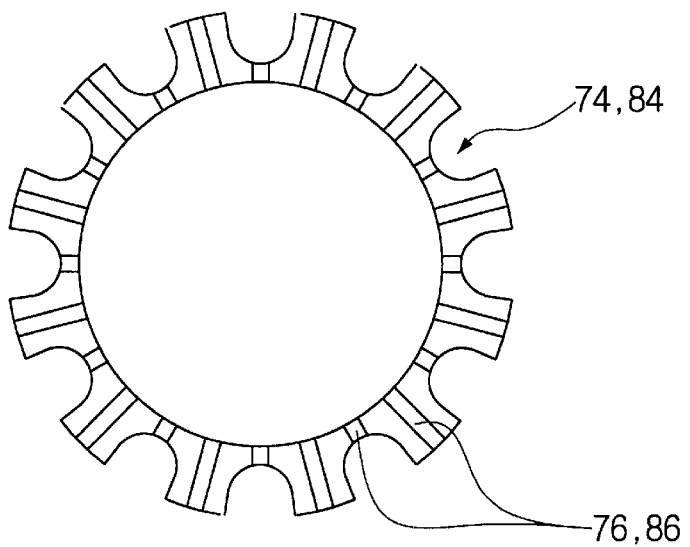
FIG. 6 is a top view illustrating a configuration of the compressing part of another embodiment of the invention.

FIG. 6 is a top view showing a configuration of the compressing part of another embodiment. In this embodiment, a plurality of cut out openings (74, 84) has "U" shapes. It is preferred to have a depth between 1.5~3.0 mm for the grooves of cut out openings (74, 84).

Figure 7:
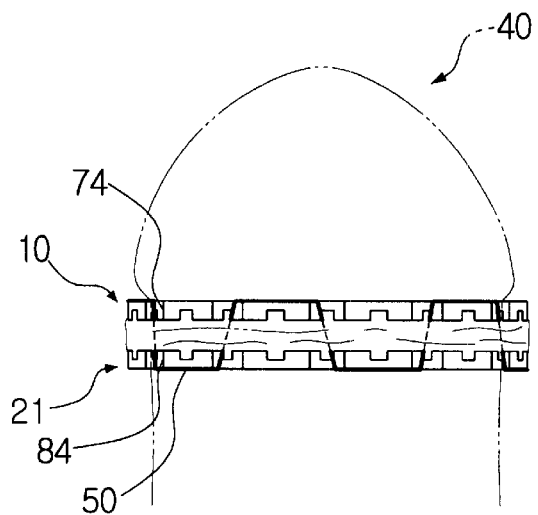
FIG. 7 shows a suturing process using another embodiment of the invention.

The process of the circumcision operation is identical to that illustrated in FIG. 2 through FIG. 4. In FIG. 7, a suturing process is shown in which the thread (50) pierces the foreskin from the upper cut out opening (74) of the second compression ring (10) to the lower cut out opening (84) of the first compression ring (20), and continues to the next stitching from the lower cut out opening (84) of the first compression ring (20) piercing through the foreskin to the upper cut out opening (74) of the second compression ring (10).

Figure 8:
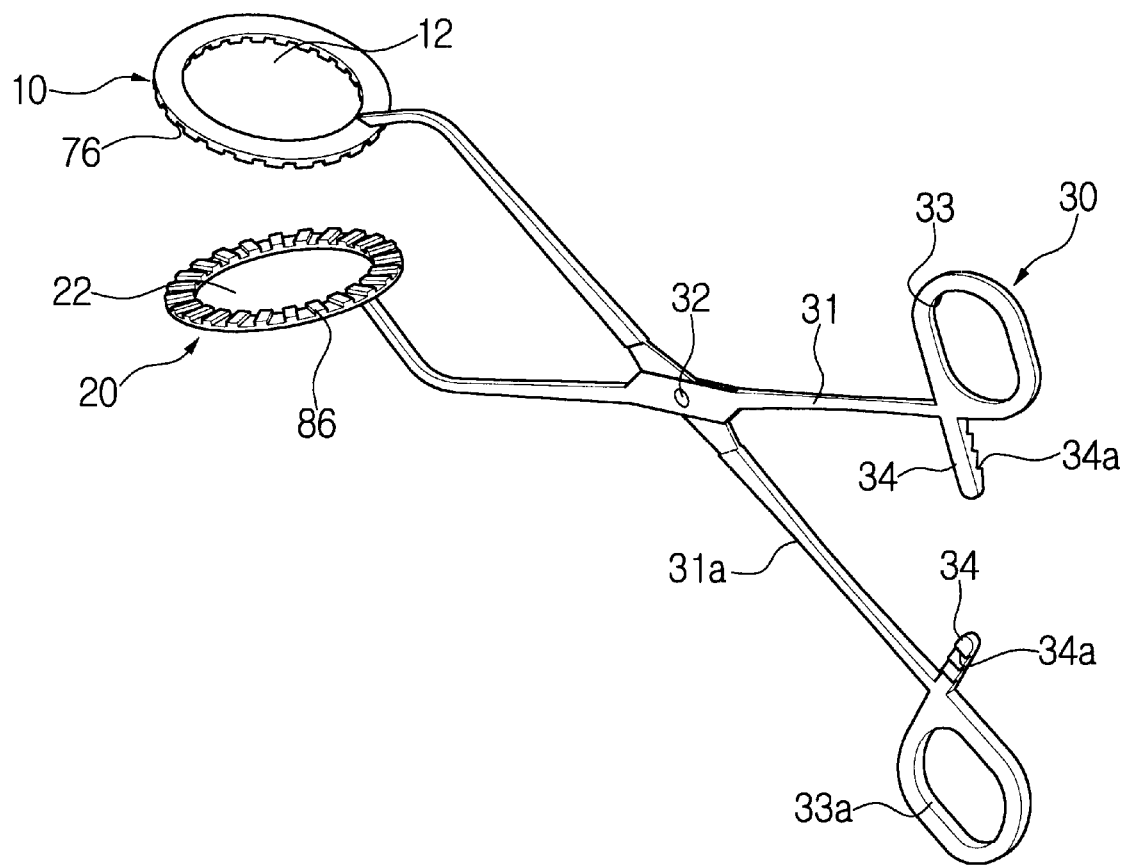
FIG. 8 is another secondary embodiment of the invention without a stitching device.

FIG. 8 is a secondary embodiment of the present invention. This embodiment has a plane shape of annular ring with a grooved inner surface. With this configuration of the circumcision clamp, the surgeon is able to freely stitch the cut edge of foreskin after trimming the excessive foreskin.

The alternative circumcision clamp of the present invention is comprised of: a pair of crossed members forms a first crossed member (31) and second crossed member (31a) having handles (30) at proximal ends. The handles (30) have a pair of finger loops.(33, 33a) and clamping tabs (34) extended from the finger loops (33, 33a), and the clamping tabs (34) contain a set of angular facets (34a). A pivot (32) is disposed at a center of the first and second crossed members for moving back and forth each other about a common axis. A pair of compression rings forms a first annular disk shaped compression ring (10) and second annular disk shaped compression ring (20). The first and second annular disk shaped compression rings (10, 20) are integrally formed on the other proximal ends of the first and second crossed members (31, 31a), respectively to mate parallel each other, so as to clamp foreskin between parallel mating surface of the first and second annular disk shaped compression rings (10, 20). The parallel mating surface of the first and second annular disk shaped compression rings (10, 20) have an anti-slip means. The anti-slip means is disposed inward of the parallel mating surface of the first and second annular disk shaped compression rings (10, 20) and comprised of a plurality of anti-slip grooves (76, 86) for preventing slipping.

Using the circumcision clamp of the present invention, it will approximately take five minutes to complete the circumcision operation. Another advantage of the present invention is that the circumcision can be performed by a surgeon or even by the patient himself.

On the other hand, the circumcision clamp is provided with various sizes of compression rings in inner diameter, thickness and width of the compressing surface and various configurations of compression rings for the different penis size of individuals such as an adult, adolescent, children or toddler. For example, the outer diameter of compression rings varies from 20~50 mm with various configurations. Accordingly, the inner diameter would be varied from 10~40 mm depending on the corresponding outer diameter. The number of stitching holes varies from 6 to 20 depending on the outer diameter of compression ring.

Therefore, the new circumcision clamp of the present invention enables one to easily perform a circumcision operation without bleeding, in order to help a patient to get rid of surgical phobia and to shorten the operating time. This clamp also has additional advantages in that: the foreskin will not slip out during an operation. A patient is able to conveniently perform a circumcision operation on his own penis by himself. The present invention provides for a cosmetically more attractive result by stitching the cut edge of foreskin accurately.

While the present invention has been described in detail with its preferred embodiments, it will be understood that further modifications are possible. The present application is therefore intended to cover any variations, uses or adaptations of the invention following the general principles thereof, and includes such departures from the present disclosure as come within known or customary practice in the art to which this invention pertains within the limits of the appended claims.

What is claimed is:

1. A circumcision clamp for clamping foreskin is comprised of:
    a pair of crossed members formed a first crossed member (31) and second crossed member (31a) having handles (30) at proximal ends,
    said handles (30) having a pair of finger loops (33, 33a) and clamping tabs (34) extended from said finger loops (33, 33a), and said clamping tabs (34) contain a set of angular facets (34a),
    a pivot (32) disposed at a center of said first and second crossed members for moving back and forth each other about a common axis,
    a pair of compression rings formed a first annular disk shaped compression ring (10) and second annular disk shaped compression ring (20), and
    said first and second annular disk shaped compression rings (10, 20) integrally formed on the other proximal ends of said first and second crossed members (31, 31a), respectively to mate parallel each other, so as to clamp foreskin between parallel mating surface of said first and second annular disk shaped compression rings (10, 20).

2. A circumcision clamp according to claim 1, wherein said first and second annular disk shaped compression rings (10, 20) further comprises a plurality of paired stitching devices having a plurality of stitching cavities with openings toward the periphery of annular rings (10, 20).

3. A circumcision clamp according to claim 2, wherein said plurality of paired stitching devices (15, 25) have a plurality of stitching holes (14, 24) and openings (14a, 24a) with spiral shape spiraling outward to the periphery of annular rings (10, 20), and said openings (14a, 24a) are positioned at opposite positions from each other.

4. A circumcision clamp according to claim 2, wherein said plurality of paired stitching devices forms a plurality of wide cut out openings (74, 84) and a plurality of protruding parts (87) being disposed between the wide cut out openings (74, 84) with a certain interval.

5. A circumcision clamp according to claim 4, wherein said wide cut out openings (74, 84) have a plurality of convex and concave guiding grooves (85) connecting to inner annular ring, wherein said protruding parts (87) have anti-slip grooves (76, 86) for preventing slipping.

6. A circumcision clamp according to claim 1, wherein said pair of first and second compression rings has varying sizes of outer diameter in ranges of 20~50 mm with various configurations, and the inner diameter of annular ring has varying sizes in a range of 10~40 mm.

7. A circumcision clamp according to claim 1, further comprises an anti-slip means having a plurality of anti-slip grooves (76, 86) for preventing slipping.

8. A circumcision clamp for clamping foreskin is comprised of:
    a pair of crossed members formed a first crossed member (31) and second crossed member (31a) having handles (30) at proximal ends,
    said handles (30) having a pair of finger loops (33, 33a) and clamping tabs (34) extended from said finger loops (33, 33a), and said clamping tabs (34) contain a set of angular facets (34a),
    a pivot (32) disposed at a center of said first and second crossed members for moving back and forth each other about a common axis,
    a pair of compression rings formed a first annular disk shaped compression ring (10) and second annular disk shaped compression ring (20),
    said first and second annular disk shaped compression rings (10, 20) integrally formed on the other proximal ends of said first and second crossed members (31, 31a), respectively to mate parallel each other, so as to clamp foreskin between parallel mating surface of said first and second annular disk shaped compression rings (10, 20), a plurality of paired stitching device having a plurality of stitching cavities or holes with openings toward the periphery of annular rings (10, 20), and said stitching device disposed on said parallel mating surface of said first annular disk shaped compression ring (10) and second annular disk shaped compression ring (20).

9. A circumcision clamp according to claim 8, wherein said plurality of paired stitching devices (15, 25) have a plurality of stitching holes (14, 24) and openings (14a, 24a) with spiral shape spiraling outward to the periphery of annular rings (10, 20), wherein said openings (14a, 24a) are positioned at opposite positions from each other.

10. A circumcision clamp according to claim 8, wherein said plurality of paired stitching devices form a plurality of wide cut out openings (74, 84) and a plurality of protruding parts (87) being disposed between the wide cut out openings (74, 84) with a certain interval.

11. A circumcision clamp according to claim 10, wherein said wide cut out openings (74, 84) have a plurality of convex and concave guiding grooves (85) connecting to inner annular ring, wherein said protruding parts (87) have anti-slip grooves (76, 86) for preventing slipping.

12. A circumcision clamp according to claim 8, wherein said pair of first and second compression rings has varying sizes of outer diameter in ranges of 20~50 mm with various configurations, and the inner diameter of annular ring has varying sizes in a range of 10~40 mm.

13. A circumcision clamp for clamping foreskin is comprised of:

a pair of crossed members formed a first crossed member (31) and second crossed member (31a) having handles (30) at proximal ends, said handles (30) having a pair of finger loops (33, 33a) and clamping tabs (34) extended from said finger loops (33, 33a), and said clamping tabs (34) contain a set of angular facets (34a), a pivot (32) disposed at a center of said first and second crossed members for moving back and forth each other about a common axis, a pair of compression rings formed a first annular disk shaped compression ring (10) and second annular disk shaped compression ring (20), said first and second annular disk shaped compression rings (10, 20) integrally formed on the other proximal ends of said first and second crossed members (31, 31a), respectively to mate parallel each other, so as to clamp foreskin between parallel mating surface of said first and second annular disk shaped compression rings (10, 20), and said parallel mating surface of said first and second annular disk shaped compression rings (10, 20) have an anti-slip means.

14. A circumcision clamp according to claim 13, wherein said anti-slip means being disposed inward of said parallel mating surface of said first and second annular disk shaped compression rings (10, 20) is comprised of a plurality of anti-slip grooves (76, 86) for preventing slipping.

15. A circumcision clamp according to claim 13, wherein said pair of first and second compression rings has varying sizes of outer diameter in ranges of 20~50 mm with various configurations, and the inner diameter of annular ring has varying sizes in a range of 10~40 mm.

* * * * *